United States Patent [19]

Kataoka et al.

[11] 4,188,725
[45] Feb. 19, 1980

[54] DENTAL HAND-PIECE WITH AN AIR TURBINE

[75] Inventors: Kenzo Kataoka, Ujl; Shoji Nakayama, Kyoto, both of Japan

[73] Assignee: Kabushiki Kaisha Morita Seisakusho, Kyoto, Japan

[21] Appl. No.: 895,742

[22] Filed: Apr. 13, 1978

[51] Int. Cl.² ............................................... A61C 1/12
[52] U.S. Cl. .................................................... 433/129
[58] Field of Search ...................... 32/27, 26; 279/1 C

[56] References Cited

U.S. PATENT DOCUMENTS 2,495,050  1/1950  Banker ................................. 279/1 C Primary Examiner—Robert Peshock
Attorney, Agent, or Firm—Koda and Androlia

[57] ABSTRACT

A dental hand-piece with an air turbine wherein a collet chuck holding a cutting tool spindle, a clamping member enough to clamp tapered chuck pawls of the collet chuck convergently from the outside, and further a moving element allowed to do the fine movement toward the outside owing to the centrifugal force acting thereon during the rotation of a rotary body are all together incorporated into the turbine rotary body supported by a shaft bearing inside a head casing, and which hand-piece is so designed in such manner that the fine movement of the moving element can provoke the sliding movement tending to clamp the chuck pawls between the collet chuck and the clamping member, is disclosed. In this hand-piece, the chuck pawls are automatically clamped at the time when the turbine rotary body starts to rotate, and the holding force of the collet chuck becomes greater to perform the reliable and steady holding of the cutting tool spindle the more high-speedily the rotary body rotates.

1 Claim, 5 Drawing Figures

DENTAL HAND-PIECE WITH AN AIR TURBINE

BACKGROUND OF THE INVENTION

1. Field of the Invention

This invention relates to a dental hand-piece for tooth cutting operation and more particularly to a hand-piece with an air turbine wherein a turbine rotary body rotating normally at about 200,000 to 500,000 r.p.m. is supported by a shaft bearing within a head casing, and is equipped with a plurality of turbine blades on its circumferential surface and a novel chucking means for a cutting tool spindle in its interior.

2. Prior Art

Dental hand-pieces with an air turbine are usually divided broadly into two categories: "air journal type" and "ball bearing type". The former is permitted to rotate at the high speed of about 200,000 to 500,000 r.p.m. normally on the ground that the friction resistance of its shaft bearing part here is infinitesimal, while the latter rotates at the low or middle speed of about 100,000 to 400,000 r.p.m. and nothing more, resulting from the fact that the same resistance increases here in one degree or another.

These types of hand-pieces incorporate in general a chucking means comprising a collet chuck with a plurality of tapered chuck pawls and a clamping member convergently clamping from the outside the chuck pawls into the inside of a turbine rotary body in such manner that the chucking means will be placed in a concentrical position with relation to the rotary body. Hereby a cutting tool spindle appears to be tightly held by the chucking means so as not to slip off. Be that as it may, there is not without any problem here. That is, it is only when the turbine rotary body is stopping that the cutting tool spindle can be firmly held in these chucking means. It becomes difficult, on the contrary, for the cutting tool spindle to be held as thoroughly and steadily as required because the holding force of the centripetal direction is weakened at the time of the high-speed rotation of the rotary body during the tooth cutting operation by the action of a great centrifugal force upon the chuck pawls of the collet chuck. Such circumstances have a very serious influence upon the dental treatment from the viewpoint of safety. Furthermore, in this type of chucking means, the fastening and unfastening operation of the clamping member is required to be done by the hand of the operator whenever the cutting tool will be replaced; this is a very annoying job.

In order to make the replacement of the cutting tool facile, another kind of hand-piece designed so as to be able to do the loading and unloading operation of the cutting tool at one touch has been developed adopting what is called "an elastic chuck" made of synthetic resin or rubber, in place of the above-mentioned chucking means. However, even with this new chucking means still remains unsolved the embarrassing problem that the centrifugal force acting on the elastic chuck leads to the reduction of the holding force of the centripetal direction while working.

As understood from the above description, it can be said that there is not developed as yet such an excellent air turbine hand-piece for dental use as to be equipped with a chucking means which is able to surely and steadily hold the cutting tool spindle at the time of the high-speed rotation of the turbine rotary body and which is highly convenient for the facile replacement of the cutting tool. Hence, there are loud cries among the persons concerned for the hoped-for development of an excellent hand-piece such as mentioned just now.

SUMMARY OF THE INVENTION

The principal object of this invention is to provide a dental hand-piece with an air turbine which is equipped with a chucking means capable of holding a cutting tool spindle all the more surely and steadily by the holding force in the centripetal direction of a collet chuck which becomes more powerful the more high-speedily a turbine rotary body rotates while working.

Another object of this invention is to provide a dental hand-piece with an air turbine including a chucking means composed of a collet chuck and a clamping member thereof wherein the loading-unloading and replacing operation of the cutting tool can be done more easily as compared with conventional elastic chucks.

A further object of the present invention is to provide a dental hand-piece with an air turbine equipped with a kind of automatic chucking device in which the holding action begins automatically as soon as a turbine rotary body starts rotating.

These and other objects and advantages of the invention will become apparent for persons skilled in the art from the following description.

DESCRIPTION OF THE PREFERRED EMBODIMENTS

It has been already tested that the aforesaid objects of this invention can be achieved by assembling the three parts: a collet chuck, a clamping member of it, and a unique moving element, which are all incorporated into a turbine rotary body in such manner that a sliding movement tending to tightly clamp the chuck pawls between the collet chuck and clamping member may be created by the fine outward movement allowed to the moving element by dint of the centrifugal force occrred at the time of the above three parts rotating together with the rotary body. For this purpose, the hand-piece according to this invention has a novel chucking means built-in within the turbine rotary body, wherein, through the movement allowed to the moving element due to the centrifugal force created at the time of the rotation of the turbine body, a force of the sliding direction (a component of the centrifugal force acting on the moving element in the sliding direction) acts on a slidable one out of either the collet chuck or clamping member, so that a sliding movement is caused between them. This sliding movement induces a force in the centripetal direction (a derivative component from the component of the centrifugal force acting on the moving element in the sliding direction) to act on the chuck pawls, thereby giving rise to the convergent clamping action of the chuck pawls.

In this way, the hand-piece according to this invention is so designed as to allow the chucking means to disperse the centrifugal force acting on the moving element in the direction of the mutual sliding between the collet chuck and clamping member, and besides in the centripetal direction, thereby these component forces cooperating with each other to function as the holding force of the chuck pawls. Accordingly, the higher the turbine rotary body rotation speed is, the greater becomes the centrifugal force acting on the moving element, therefrom leading to the strengthening of the holding force of the chuck pawls to enable the cutting tool spindle to be held more reliably and steadily. In addition, the holding force of the chuck pawls becomes almost equal to zero at the resting time of the turbine rotary body, so that the loading-unloading and replacing operation of the cutting tool can be conducted more easily with the last trouble beyond comparison with conventional elastic chucks. Further, in the hand-piece according to this invention, as soon as the turbine rotary body begins to rotate, the chuck pawls comes to be convergently clamped automatically to hold the cutting tool spindle. Therefore, the operator is wholly released from the annoying job that he is bound to do the troublesome hand operation of clamping and loosening the clamping member each time of loading and unloading the cutting tool, as seen in the case with conventional hand-pieces provided with old-fashioned chucking means consisting of only collet chuck and clamping member.

Figure 1:
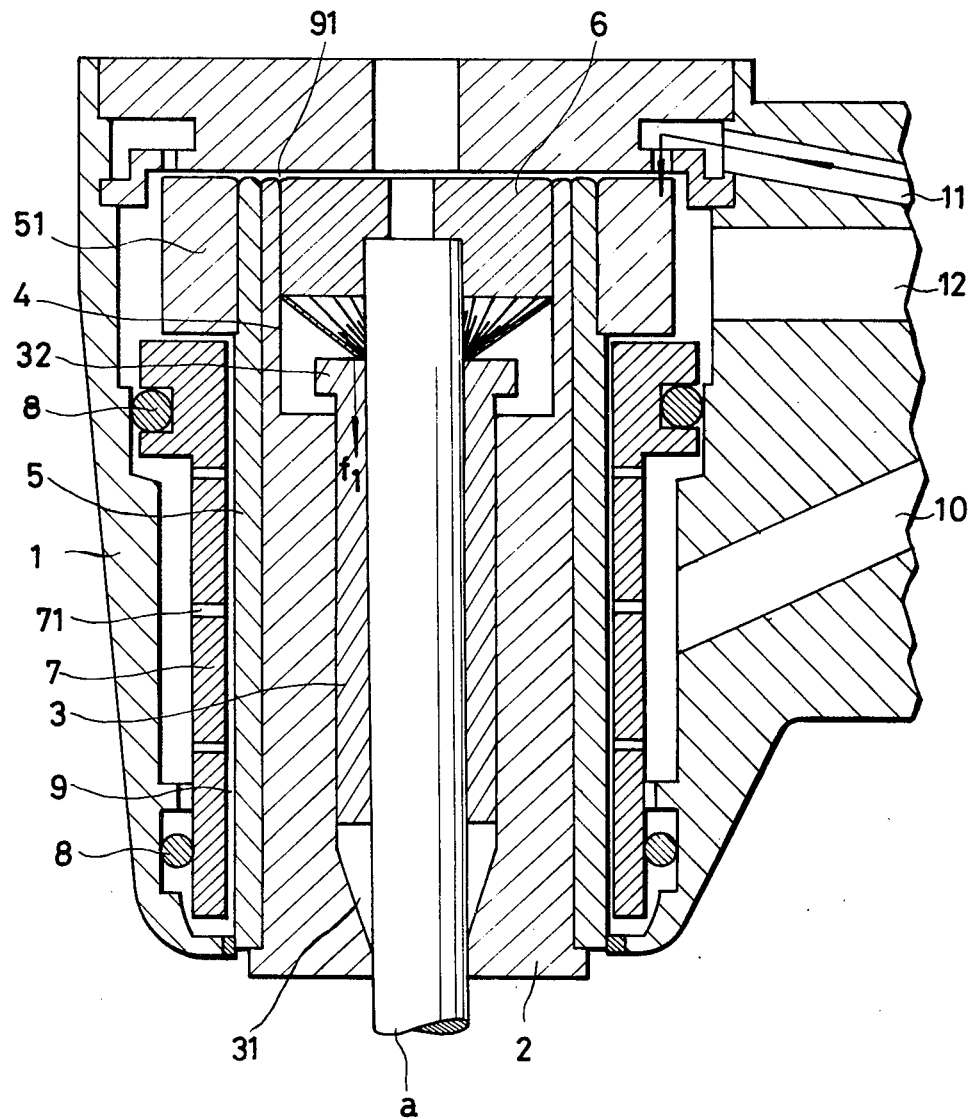
FIG. 1 is a vertical sectional view in part showing the head part of an embodiment of the hand-piece of the present invention.
Figure 2:
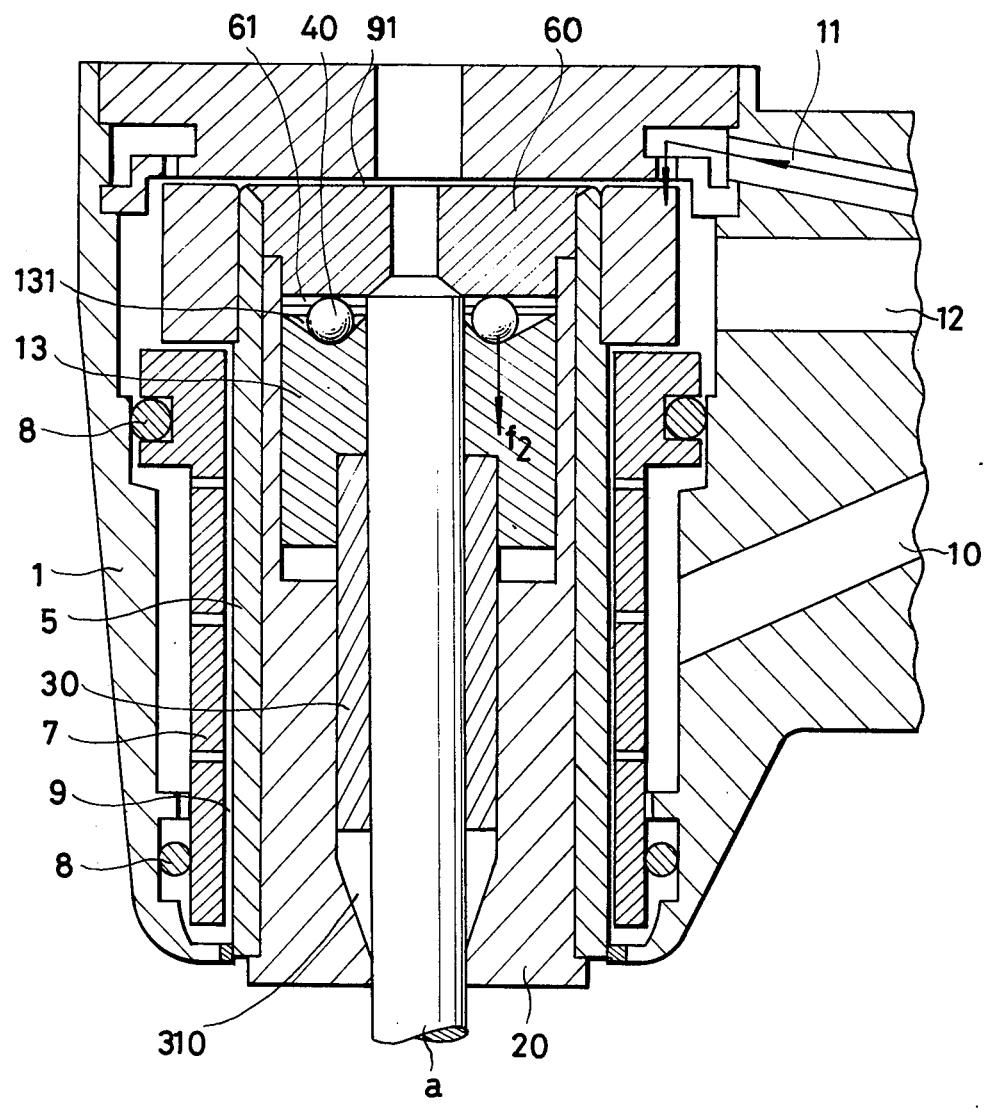
FIG. 2 is a vertical sectional view in part showing the head part of another embodiment of the hand-piece of the present invention.

The hand-piece according to this invention is divided broadly into categories: the one of a type wherein a collet chuck is inserted slidably in the thrusting direction into a clamping member having an immovable connection with a turbine rotary body, and wherein a sliding movement is caused between the collet chuck and clamping member by the action of a force of the inserting direction of the collet chuck (to be more exact, a component of the inserting direction dispersed from the centrifugal force acting on a moving element) on the collet chuck through the movement of the moving element; this type is hereinafter referred to as "type A"; and the other of a type wherein, in the contrast with the above, the clamping member is put in a movable connection with the turbine rotary body in the thrusting direction, while the collet chuck inserted in the thrusting direction is set in an immovable relation to the clamping member, and wherein a sliding movement is caused between the clamping member and collet chuck by the action of a force of the direction opposed to the inserting direction of the collet chuck (to say more precisely, a component of the direction opposed to the inserting direction dispersed from the centrifugal force acting on the moving element) on the clamping member through the movement of the moving element; this type is hereinafter called as "type B". Either of these types must be designed in such manner that the centrifugal force acting on the moving element will be greater than that on the pawls of the collet chuck. The reason is that in case of the reversion of the relative proportion in the centrifugal force, the movement of the moving element through the centrifugal force would be arrested, the mutual sliding movement between the collet chuck and clamping member could not be caused, and the convergent clamping action of the chuck pawls would be made unworkable. FIGS. 1 and 2 show an embodiment of type A, and FIG. 3 an embodiment of type B. Description will now be directed to the hand-piece according to this invention with reference to the accompanying drawings.

Figure 4:
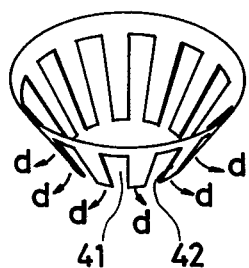
FIG. 4 is a perspective view showing an embodiment of a moving element adopted into this invention.
Figure 5:
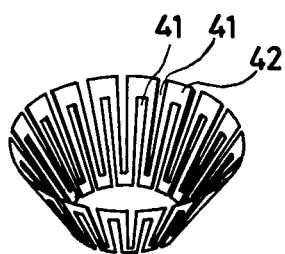
FIG. 5 is a perspective view showing another embodiment of a moving element adopted into this invention.

FIG. 1 is an embodiment of type A in which the force of the inserting direction directly acts on the collet chuck during the movement of the moving element. In this case, the clamping member 2 which also serves as a chuck case is concentrically fit and fixed within the turbine rotary body 5, and the collet chuck 3 in turn is inserted into the clamping member concentrically and slidably in the thrusting direction. This collet chuck 3 is provided at its front part with a plurality of chuck pawls 31 tapering forward and having a number of uniformly cut apart parts, and is formed into a flange 32 at its rear end. The moving element 4 is held between the chuck 4 and a stopper 6 of the cutting tool spindle a in such a stationary state as to be located in a relative position concentrical with the axis of the cutting tool spindle a. The moving element 4 in this embodiment is a polipetalous elastic ring having a plurality of split grooves 41 cut-out from the small diameter side, as shown in FIG. 4, and all petals 42 of it do the efflorescing motion in the direction of the narrows by dint of the centrifugal force during the rotation. This elastic ring impinges against the flange 32 of the collet chuck 3 at its small diameter side, and against the stopper 6 at its large diameter side, respectively. In place of such a type of elastic ring, it is of course permissible to employ another type of polypetalous elastic ring which is provided with split grooves 41 cut apart alternately from both sides of the small and large diameters, as shown in FIG. 5, or other types similar to this. In such a case, however, careful consideration should be paid to the fixing procedure of the large diameter side on the stopper 6 in order to enable the moving element 4 to perform reliably the efflorescing motion, for example, either by fixing the large diameter side of the elastic ring into the corner formed by the stopper 6 and the clamping member 2 which also serves as the chuck case and is made at its inner diameter in size equal to the large diameter of the elastic ring, as shown in FIG. 1, or by providing a suitable groove or member for fixing the elastic ring on the impinging face of the stopper 6.

Except that a chucking means of such a specially designed structure as the above-mentioned is housed in the turbine rotary body 5, the hand-piece in FIG. 1 has almost the same structure as that of conventional hand-pieces of an air journal type. To be more precise, in this hand-piece, a bearing 7 having a plurality of through-holes is loaded within the head casing 1 through the medium of a pair of O-rings 8,8. Inside this bearing 7 is floatingly set the turbine rotary body 5 having a plurality of turbine blades 51 with a radial gap 9 between. This turbine rotary body 5 is supported with the application of air bearing consisting of compressed air supplied from an outer air compressor (not shown) through an air inlet 10 and the through-holes 71 to the radial gap 9, and partially through an air inlet 11 to a thrust gap 91, thereby being capable of doing the high-speed rotation of 200,000 to 500,000 r.p.m. in a no-load state while receiving a great portion of compressed air jetted out of the air inlet 11 upon the turbine blades 51. Most of compressed air supplied through the air inlets 10, 11 comes to be discharged from air exhaust pipe 12 outward.

When the turbine rotary body 5 rotates at such a high speed, then the cutting tool spindle a, the clamping member 2, the collet chuck 3, the moving element 4 comprised of the polypetalous elastic ring, and the stopper 6 all rotate in concert with the rotary body; and consequently each of them are subjected to the centrifugal force. Among them, however, only the moving element, which is allowed to do the efflorescing motion toward the outside by dint of the then centrifugal force, has the ability of conducting the locomotion. The centrifugal force acting on the moving element 4 is dispersed into a component in the inserting (thrusting) direction of the collet chuck 3 at the impinging face of the flange 32 thereof. The chuck 3 is then compressed by this component force $f_1$ in the inseting direction to slide along the inner side of the clamping member 2. Through this sliding, the component force $f_1$ is dispersed further into another component force in the centripetal direction at the tapered face of the chuck pawls 31 to act thereon, giving rise to the convergent clamping motion of the chuck pawls 31. The hand-piece is thus provided with such a chucking means that can disperse the centrifugal force acting on the moving element 4 into a component force in the thrusting direction and then into another component force in the centripetal direction and can make the thus-created centripetal component force act on the chuck pawls 31. When the turbine rotary body 5 begins to rotate, the chucking means works automatically. The higher the rotary body 5 rotation is, the more vigorous becomes the holding power of the chuck pawls 31, being able to hold the cutting tool spindle more reliably and steadily. It will be also easily understood that the loading-unloading and replacing job of the cutting tool can be done at one touch and without any trouble because the holding power of the chuck pawls 31 becomes equal to nothing at the resting time of the turbine rotary body 5.

FIG. 2 shows an embodiment of the hand-piece of type A, wherein a force of the inserting direction attributable to the movement of the moving element acts on the collet chuck indirectly through an auxiliary member. In this hand-piece which is nearly like one in FIG. 1, a clamping member 20 which also serves as a chuck case is set and secured concentrically inside the turbine rotary body 5. Into this clamping member 20 is inserted a collet chuck 30 provided at its front part with the same chuck pawls 310 as the above-mentioned one 31 concentrically and slidably in the thrusting direction. Between the rear end of the chuck 30 and the circumferential wall at the rear end of the clamping member 20, the auxiliary member 13 is fit in slidably in the thrusting direction from backside. And between this auxiliary member 13 and a stopper 60, a moving element 40 comprised of a plurality of balls is arranged at regular intervals around the cutting tool spindle a. These balls are kept in a shallow circumferential groove 131 of a somewhat V-shaped cross section which is formed on the auxiliary member 13 so as to be able to move radially along guide grooves 61 formed radially on the impinging face of the stopper 60 while compressing the auxiliary member 13 when the centrifugal force actuates them at the time of the rotation of the turbine rotary body 5. The structure other than the above-stated do not much differ from those of the hand-piece in FIG. 1.

When the balls 40 are allowed to move radially by dint of the centrifugal force working during the rotation of the turbine rotary body 5, the centrifugal force acting on the balls 40 is dispersed partially into a component of the inserting (thrusting) direction of the collet chuck 30 at the bottom of the circumferential groove 131 of the auxiliary member 13. The thus-created component force $f_2$ is transferred through the medium of the auxiliary member 13 and compresses the collet chuck 30 in its inseting direction, thereby the collet chuck 30 being forced to slide along the inner face of the clamping member 20. This sliding movement causes the component force $f_2$ to be dispersed further partially into another component force of the centripetal direction at the tapered face of the chuck pawls 310. The action of this latter component force on the chuck pawls 30 conduces to the convergent clamping motion of the chuck pawls 310. Accordingly, this hand-piece also is effective as excellently as the one in FIG. 1.

Figure 3:
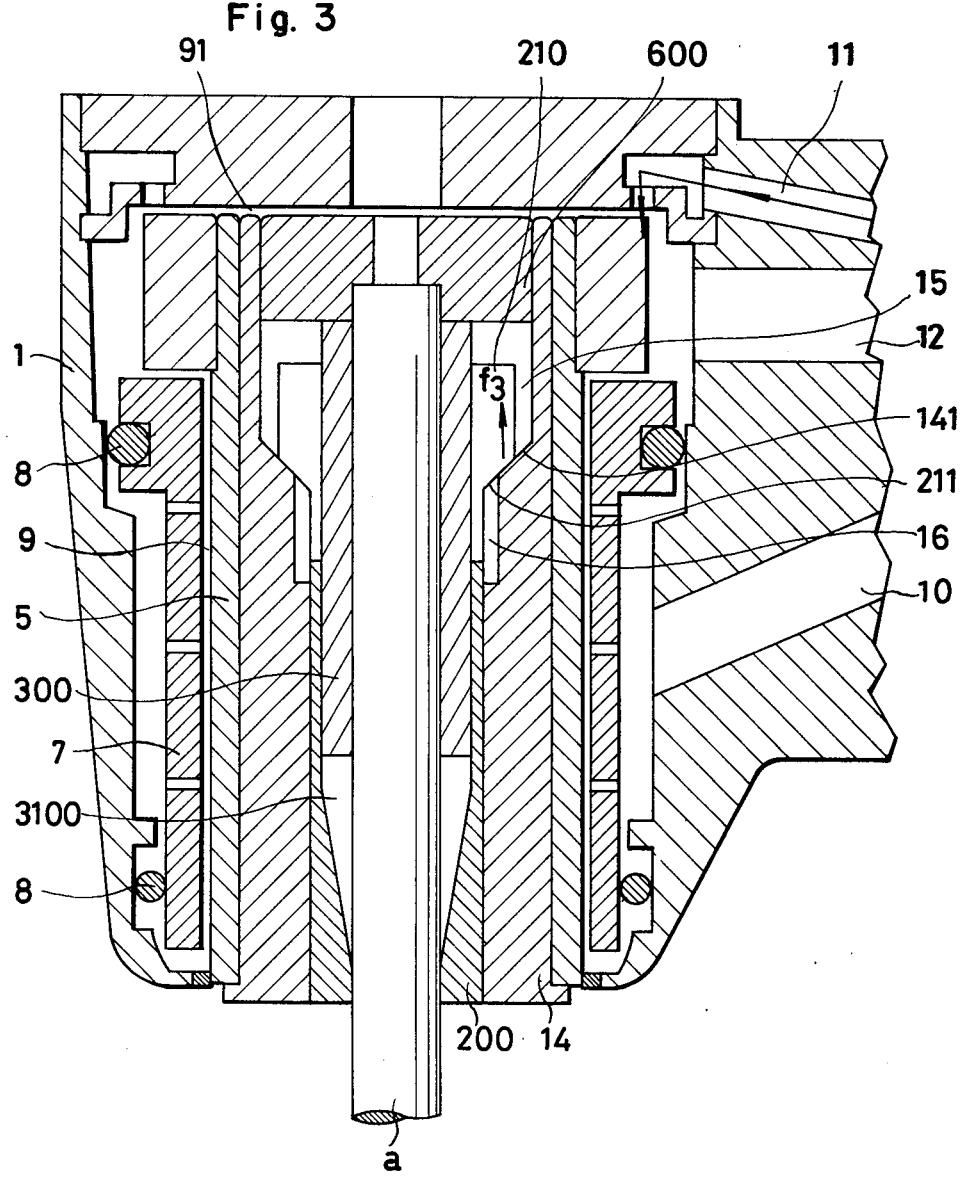
FIG. 3 is a vertical sectional view in part showing the head part of another embodiment of the hand-piece of the present invention.

FIG. 3 shows an embodiment on type B, wherein a chuck case 14 is concentrically fit in and fixed within the turbine rotary body 5. Into this chuck case 14 is inserted a clamping member 200 slidably in the insertion direction and concentrically with the turbine rotary body 5. The clamping member 200 is formed into a somewhat cylindrical one provided at its one end part (in the Figure: rear end part) with an expanding part 210 having a plurality of cut-out slits and inside at its other end part (in the Figure: front and end part) with a tapered face for clamping chuck pawls 3100. The expanding part 210 with the cut-out slits constitutes a moving element capable of doing the efflorescing movement with the help of the centrifugal force. Between the moving element-constituting part of the clamping member 200 and the chuck case 14 are formed spaces 15, 16 for allowing the moving element to do the efflorescing motion. Both shoulder 141 of the chuck case 14 which engages the expanding part 210 and the engaged face of the latter are made tapered obversely or reversely in order to be able to disperse the centrifugal force in the thrusting direction. Into this clamping member 200 of such a unique construction is inserted the same collet chuck 300 as the collet chuck 30 shown in FIG. 2 in the thrusting direction from one side where the expanded part 210 of the clamping member 200 is formed, and the rear end of the collet chuck 300 is fixed on the stopper 600 after having been impinged thereagainst. Description about the other constructions of it may be omitted for the reason that they are wholly equal to those of the hand-piece in FIG. 1.

When the expanding part, i.e., moving element 210 of the clamping member 200 is allowed to do the efflorescing movement by dint of the centrifugal force working during the rotation of the turbine rotary body 5, the centrifugal force acting on the expanding part 210 is dispersed into two components in the inserting direction and in the counter direction of the collet chuck 300 at the tapered shoulder 141 of the chuck case 14. The clamping member 200 is pulled up in the counter direction by the component force $f_3$ to slide up over the circumferential face of the collet chuck 300. With this sliding movement is dispersed the component force $f_3$ partially further into another component force in the centripetal direction at the tapered face of the chuck pawls 3100. The action of this component force on the chuck pawls 3100 conduces to the convergent clamping motion of the latter 3100.

In the hand-piece according to the invention, it will be understood from the above description that the holding force of the chuck pawls can be more powerful the larger the radius of gyration and the mass of the moving element is made up and the more the number of revolution is increased. To give an example, in the hand-piece illustrated in FIG. 2, when eight steel balls of 1.0 mm in diameter and 0.0041 g in weight are arranged around the cutting tool spindle a at 2.8 mm distance from its axis at regular intervals, it is possible to cause the component force of the sliding direction of 3 to 18 kg/cm$^2$ to act on the chuck pawls in the range of the rotational frequency of the turbine rotary body of 200,000 to 500,000 r.p.m. depending on the variation of the inclination of the circumferential groove 131.

While three embodiments of the hand-piece according to the present invention have been described above with reference to the accompanying drawings, it will be now easily understood by those skilled in the art that the present invention is not limited to these embodiment and that all sorts of modifications may be made without departing from the scope of the claims of this invention.

We claim:

1. A dental hand-piece with an air turbine wherein a collet chuck holding a cutting tool spindle and a clamping member, which stands in immovable relation to a turbine rotary body, enough to clamp tapered chuck pawls of said collet chuck convergantly from the outside are incorporated into said rotary body supported by a shaft bearing inside a head casing in such a relative position that said collet chuck and said clamping member will be set concentrically and movably in the thrusting direction with said rotary body inside which further a moving element, said moving element is a polypetalous elastic ring having a plurality of split grooves cut out, to say the least, from the small diameter side, maintaining a relative position concentrically with the axis of said cutting tool spindle is kept in a stationary state during the down-time, but comes to be allowed to do the fine efflorescing movement toward the outside owing to the centrifugal force acting thereon during its rotating together with said rotary body, and said handpiece is characterized by being designed in such manner that the efflorescent movement of said moving element with the help of said centrifugal force can provoke the sliding movement tending to compress said collet chuck and clamp convergently said chuck pawls between said collet chuck and said clamping member.

* * * * *